United States Patent [19]
Fang et al.

[11] Patent Number: 6,133,746
[45] Date of Patent: Oct. 17, 2000

[54] METHOD FOR DETERMINING A RELIABLE OXIDE THICKNESS

[75] Inventors: Peng Fang, San Jose; Hao Fang, Cupertino, both of Calif.

[73] Assignee: Advanced Micro Devices, Inc., Sunnyvale, Calif.

[21] Appl. No.: 09/163,414

[22] Filed: Sep. 30, 1998

[51] Int. Cl.[7] .......................... G01N 27/92; G01R 31/12; H01L 21/66
[52] U.S. Cl. ............................ 324/769; 324/766; 438/14
[58] Field of Search ...................... 324/765, 766, 324/769, 719; 438/14, 17

[56] References Cited

U.S. PATENT DOCUMENTS

| | | | |
|---|---|---|---|
| 5,548,224 | 8/1996 | Gabriel et al. | 324/765 |
| 5,650,336 | 7/1997 | Eriguchi et al. | 324/719 |
| 5,793,212 | 8/1998 | Om | 324/765 |
| 5,801,538 | 9/1998 | Kwon | 324/671 |

*Primary Examiner*—Glenn W. Brown

[57] ABSTRACT

A method for determining a reliable gate oxide thickness for a transistor involves subjecting test transistors to an alternating current (AC) voltage until the test transistors break down. The breakdown times of the test transistors are measured and correlated with the corresponding gate oxide thickness of the test transistor to form a reliability model of the transistor. The reliable gate oxide thickness is determined by extrapolating the reliability model out to a predetermined period of time for which reliability is desired, for example, ten years.

10 Claims, 3 Drawing Sheets

METHOD FOR DETERMINING A RELIABLE OXIDE THICKNESS

FIELD OF THE INVENTION

The present invention relates to non-volatile semiconductor flash memory devices and, more particularly, to a method for determining a reliable oxide thickness for a high-voltage transistor in a flash memory device.

BACKGROUND OF THE INVENTION

Conventional flash memory systems, otherwise known as flash electrically erasable programmable read only memories (FLASH EEPROMs), typically include a two-dimensional array of floating gate memory transistors, or "cells," formed on a semiconductor substrate. These cells are arranged into strings, known as NAND strings, to form bit lines, wherein each cell is coupled to the next cell in the string by coupling the source of one transistor to the drain of another transistor. Word lines, disposed perpendicularly to the bit lines, connect to the control gate of one transistor in each NAND string.

Initially, the cells in a flash memory are erased so that the floating gate memory transistors have a certain threshold voltage, such as −2V. Selected cells are programmed to a higher threshold voltage by applying a high voltage, such as 18V–23V, for a period of time, such as about 200 μs, to the word lines of the selected cells. This voltage is typically controlled through a high voltage transistor on the periphery of the memory device. Flash memory devices are attractive in application environments requiring more frequent programming than an EPROM but needing to be updated less often than typical main memory, cache, or registers (i.e., DRAM or SRAM).

Therefore, operation of a NAND flash memory requires a high voltage transistor that can reliably support occasional voltages up to 23V. Referring to FIG. 5, a high-voltage transistor used in a flash memory device is formed on a substrate 500 and electrically isolated by isolation structures 502, which may be formed by Local Oxidation of Silicon (LOCOS), trench isolation, or other such techniques. The high-voltage transistor includes a doped source region 504 and a doped drain region 506 separated by a channel region 508. A gate oxide 510 is formed over the channel region 508 to insulate the gate electrode 510 from the channel region 508. The high voltage transistor also includes a source electrode 514 and a drain electrode 516, coupled to the source region 504 and the drain region 506 respectively.

The high voltage across the transistor, however, causes a grave concern for the reliability of the transistor. A common failure scenario for a field effect transistor is a breakdown in the gate oxide 510 of the transistor, usually involving carriers injected into the gate oxide 510. An important carrier-injection mechanism is a cold carrier injection phenomenon known as Fowler-Norheim tunneling, which is more pronounced for higher gate voltages and thinner gate oxides.

Consequently, a conventional approach for determining the reliability of a transistor is to stress gate oxides of varying thicknesses under direct current (DC) conditions and project the gate oxide reliability for an industry standard ten-year lifetime. Specifically, test structures including transistors with several thin gate oxides, respectively, are manufactured, and subjected to a DC voltage until the transistors break down. The time to breakdown for the device with the thin gate oxides is measured, and the gate oxide thickness for a ten-year lifetime is extrapolated from the respective breakdown times. By this reliability criterion, the oxide thickness sufficient to meet the ten-year lifetime under the DC stress conditions is selected as the minimum gate oxide thickness for the transistor. This approach typically results in gate oxide 510 thicknesses of about 400–500 Å being chosen.

From a performance point of view, however, a thinner gate oxide is preferred if the reliability concerns can be met. For example, a thinner gate oxide results in an increased drive current, which improves switching speed. As another example, a thinner gate oxide leads to a shallower junction depth, providing greater control over short channel effects affecting the threshold voltage ($V_T$) of the transistor. For yet another example, a thinner gate oxide fosters a smaller gate delay and, hence, faster device performance.

SUMMARY OF THE INVENTION

There exists a need for obtaining thinner gate oxides in high voltage transistors, especially in high voltage transistors used in flash memory circuits, while ensuring that the transistor device reliably operates for an industry-standard ten years.

This and other needs are addressed by the present invention in which the reliability data for a transistor is generated by subjecting test transistors to an alternating current (AC) stress test. Since a constant DC voltage stresses the gate oxide of a transistor much more than an alternating current, the conventional methodology overestimates the required thickness of a reliable gate oxide for transistors that are not normally subjected to a constant DC voltage, such as a high-voltage transistor in a flash memory device.

Accordingly, one aspect of the invention relates to a method for determining a reliable gate oxide thickness for a transistor to be fabricated according to a fabrication technology. The method includes the step of fabricating test structures according to the fabrication technology, in which the test structures include a test transistor having a gate oxide of one of a set of predetermined thicknesses. An alternating voltage is applied to stress the test transistors, from which reliability data, such as breakdown times, are measured. Based on the measured reliability data, a reliable gate oxide thickness is determined.

Additional advantages and novel features of the present invention will be set forth in part in the description that follows, and in part, will become apparent upon examination or may be learned by practice of the invention. The advantages of the invention may be realized and obtained by means of the instrumentalities and combinations particularly pointed out in the appended claims.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF THE PREFERRED EMBODIMENT

A method for determining a gate oxide thickness of a high-voltage transistor in a flash memory device is described. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

The present invention stems from the realization that the conventional DC stress model is inappropriate for transistors that normally operate with an alternating voltage, because a constant (DC) voltage stresses the transistor much more than an alternating (AC) voltage whose peak amplitude is at the same voltage level as the constant voltage. Therefore, it is more realistic to calculate the reliability of a gate oxide manufactured to a certain thickness based on AC stress conditions, under which the transistor normally operates.

One example of such a transistor, for which the present invention is particularly advantageous, is a high-voltage transistor in a flash memory device. The flash memory high-voltage transistor is used in programming flash memory cells and, thus, is not constantly stressed at the highest voltage. In some implementations of a flash memory system, in fact, the programming voltage is not even constant during programming, but applied as a series of pulses. Consequently, since these high-voltage transistors in a flash memory device normally operate under AC conditions, the reliability data collected for such transistors are generated under AC stress conditions in the present invention.

Figure 1:
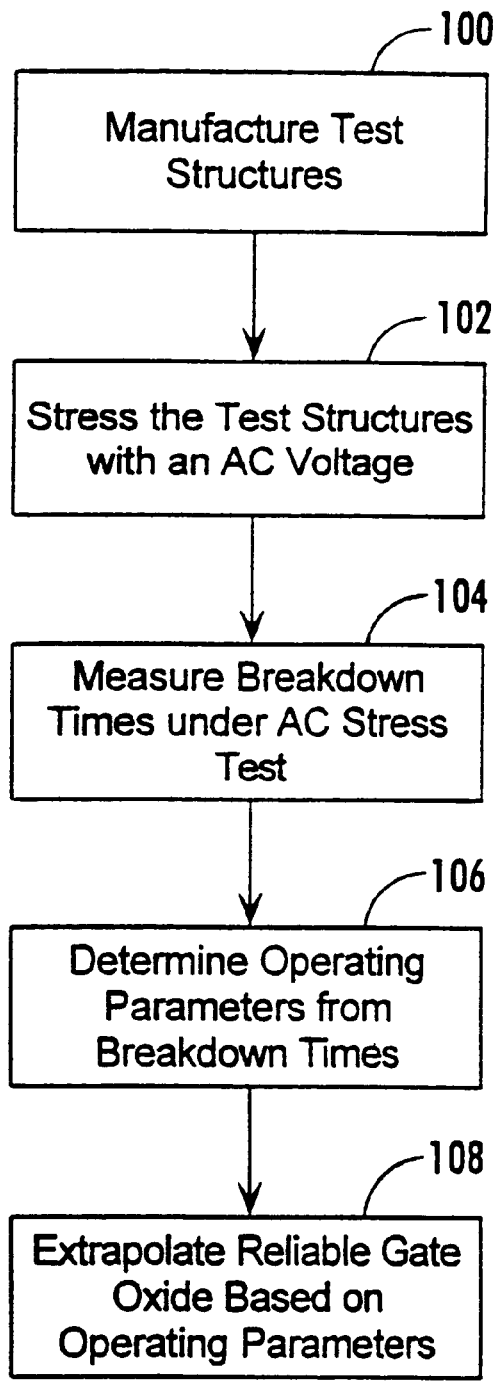
FIG. 1 is a flowchart showing a method for determining a reliable gate oxide.

FIG. 1 is a flowchart illustrating a method for determining a reliable gate oxide of a desired transistor according to an embodiment. In step 100, a number of test structures are manufactured according to the fabrication technology and the design rule of the desired transistor. Each test structure contains at least one transistor of the same dimensions as the desired transistor, except the gate oxide is much thinner. Use of a thinner gate oxide results in breakdown times under the stress test to be measurable within a reasonable amount of time (e.g. a week) instead of ten years. The thickness of the gate oxide preferably ranges from about 20 times to about 4 times smaller than the thickness predicted for the desired transistor under DC stress conditions. For example, if a reliable gate oxide thickness for a transistor according to a 23V DC stress test is about 400 Å, the determination of a gate oxide thickness for the test transistors under an AC stress test conducted should be in the range of 20 Å to 80 Å.

Figure 2:
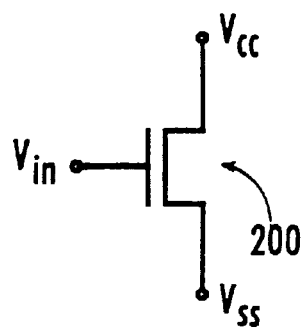
FIG. 2 depicts a high-voltage transistor used as a test structure.
Figure 3:
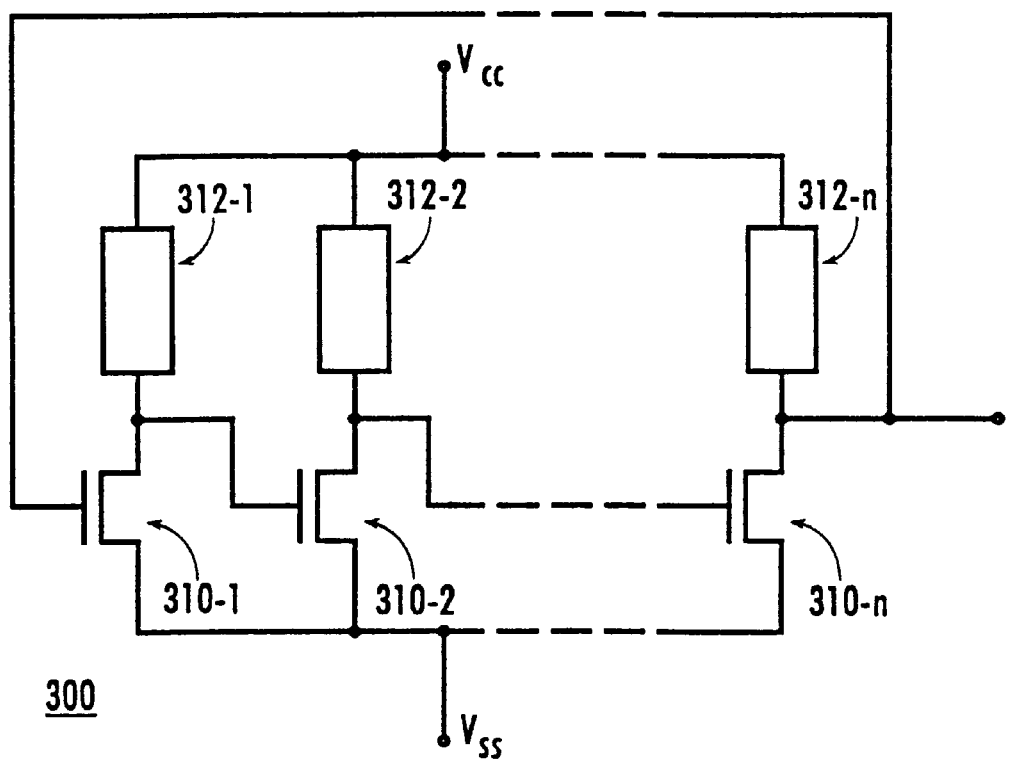
FIG. 3 depicts a ring oscillator used as a test structure.

In one embodiment, the test structure consists of a single transistor 200, shown in FIG. 2. In another embodiment, the test structure includes a ring oscillator 300 comprising many test transistors, schematically illustrated in FIG. 3. Referring to FIG. 3, depicted are portions of an n-stage simple inverter based ring oscillator 300, where n is any odd number such as 71, 91, and 101. Each stage of the ring oscillator comprises a simple inverter. For example, the first stage comprises an NMOS transistor 310-1 and a load 312-1. Likewise, the other ring oscillator stages, from the second stage through the last stage, comprise NMOS transistors 310-2 through 310-n and loads 312-2 to 312-n, respectively. The load 314 may be a resistor, a depletion mode transistor, or, as in CMOS, a PMOS transistor having a gate (not shown) coupled to the gate of the respective NMOS transistor 310. The gate oxide thickness of the NMOS transistors 310 of ring oscillator 300 are the same. However, other ring oscillators in the batch may employ NMOS transistors having a different, common gate oxide thickness.

In step 102, the test structure is subjected to an AC stress test until the test structure undergoes a failure. In the case of the test structure depicted in FIG. 2, an AC input voltage $V_{in}$ is applied to the gate of transistor 200. The AC input voltage $V_{in}$ ranges from 0V to a peak amplitude of at least 18V, for example, about 22V, about 23V, or in between. The DC supply voltage $V_{CC}$, moreover, is preferably the same as the peak amplitude of the AC input voltage $V_{in}$, i.e., at least 18V, for example, from about 22V to about 23V.

In one embodiment, the AC input voltage $V_{in}$ has a duty cycle that is at most 50% such as 33%, to reflect the fact the high-voltage transistor in a flash memory system is not always operating at the highest voltage. To account for flash memory devices in which the memory cells are programmed by a series of pulses, the input voltage $V_{in}$, in another embodiment, is applied as a series of pulses (e.g., square waves), each pulse having a duration of between 3 µs to about 11 µs with about 3 µs to about 4 µs between pulses. In the embodiment depicted in FIG. 3, each inverter of the ring oscillator 300 receives a common supply voltage $V_{CC}$, also at least 18V, for example, from about 22V to about 23V, and each inverter in the ring oscillator is, therefore, subjected to a voltage that swings from ground to the supply voltage $V_{CC}$.

Figure 5:
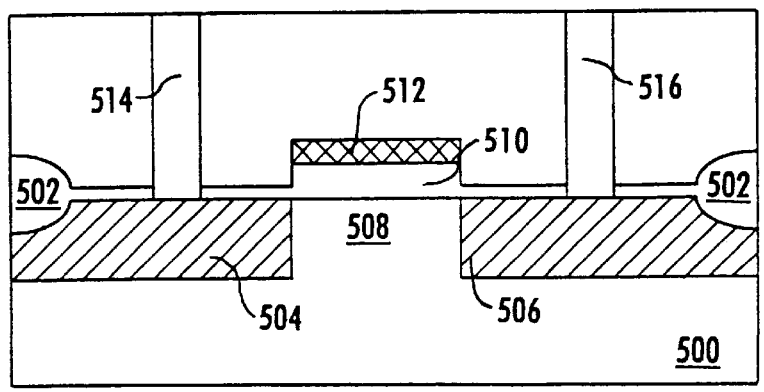
FIG. 5 depicts a cross-section of a high-voltage transistor.

The time for which the test structures are subjected to the AC stress voltage is measured until the test structure breaks down (step 104). Referring to FIG. 5, a break down typically occurs in the gate oxide 510, resulting in a short circuit from gate electrode 512 to source region 504. To account for variations in manufacturing the test structures, multiple experiments may be performed with several samples of the same gate oxide thickness to generate an average breakdown time. The breakdown times constitute the measured reliability data and are correlated with the gate oxide thickness of the test transistor in the test structures to ascertain the reliable gate oxide thickness for a ten-year lifetime, as described hereinafter.

In step 106, reliability parameters for the desired transistors are determined from the reliability data, such as the measured breakdown times. The breakdown time of a gate oxide can be modeled by the equation:

$$\tau_{BD} = \tau_0 \exp(A t_{ox}), \tag{1}$$

where $\tau_{BD}$ is the breakdown time of the gate oxide, $\tau_0$ is a pre-exponential factor, exp is the exponential function [exp $(x)=e^x$], A is an empirical parameter, and $t_{ox}$ is the thickness of the gate oxide. Thus, the reliability parameters $\tau_0$ and A are determined from the measured breakdown times $\tau_{BD}$ and their corresponding gate oxide thickness $t_{ox}$.

Figure 4:
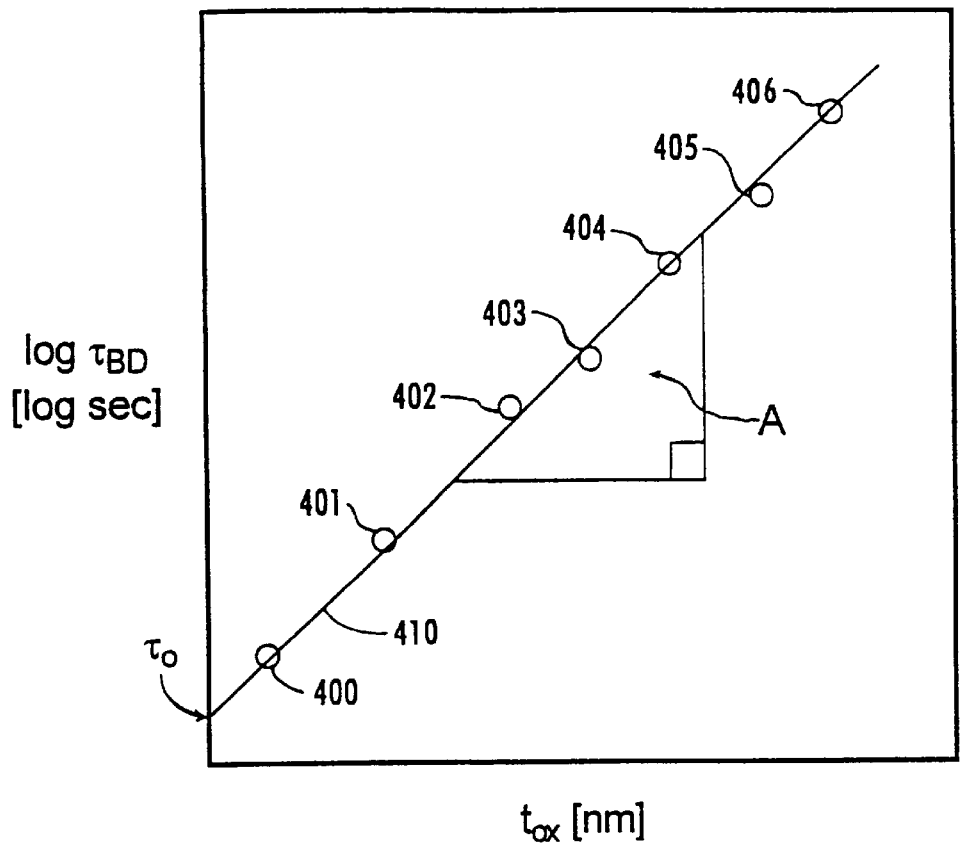
FIG. 4 is a graph illustrating a log-relationship between measured breakdown times and gate oxide thickness.

One way to determine the reliability parameters is to plot the logarithm of the breakdown times $\tau_{BD}$ on a graph against the corresponding gate oxide thickness $t_{ox}$. FIG. 4 is a graph of an exemplary set of AC stress tests, wherein each point 400 to 406 on the graph corresponds to an AC stress test. A best-fit line 410 through the points 400 to 406 is calculated, for example, by a least-squares approximation. The best-fit line 410 is extrapolated to intercept the $\tau_{BD}$-axis to obtain the pre-exponential factor $\tau_0$. The slope of the best-fit line 410 is calculated to determine the A empirical parameters. It is evident that these steps can be all performed by a computer without plotting the graph, for example by manipulating equation (1) with the experimental reliability data $\tau_{BD}$ and $t_{ox}$.

When the reliability parameters $\tau_0$ and A have been determined, the gate oxide for a ten-year lifetime is calculated therefrom (step 108). In one embodiment, the reliable gate oxide is calculated from the inverse of equation (1), namely:

$$t_{ox} = \frac{1}{A} \ln \frac{\tau}{\tau_0}, \qquad (2)$$

where $\tau$ is the desired lifetime, e.g. 10 years or $3.1 \times 10^8$ sec. This calculation can also be performed by a suitably programmed general purpose computer or an electronic calculator.

By conducting a stress test with an AC voltage instead of a DC voltage, a more realistic (and thinner) reliable gate oxide is determined. While ensuring an adequate gate oxide thickness that will be reliable to meet industry-standard requirements, the thickness of the gate oxide can be made smaller, thereby improving the performance of the transistor. For example, a thinner gate oxide results in an increased drive current, improving switching speed. A thinner gate oxide leads to a shallower junction depth, providing greater control over short channel effects affecting the threshold voltage ($V_T$) of the transistor. Furthermore, a thinner gate oxide fosters a smaller gate delay and, hence, faster device performance.

While this invention has been described in connection with what is presently considered to be the most practical and preferred embodiment, it is to be understood that the invention is not limited to the disclosed embodiment, but on the contrary, is intended to cover various modifications and equivalent arrangements included within the spirit and scope of the appended claims.

What is claimed is:

1. A method for determining a reliable gate oxide thickness for a transistor to be fabricated according to a fabrication technology, the method comprising the steps of:

fabricating a plurality of test structures according to the fabrication technology, wherein the test structures include test transistors, each test transistor having a gate oxide of one of a plurality of thicknesses;

applying an alternating voltage to stress the test transistors;

measuring reliability data from results of applying the alternating voltage; and determining a reliable gate oxide thickness based upon the measured reliability data.

2. The method of claim 1, wherein the step of measuring reliability data includes the step of measuring periods of time for which the alternating voltage is applied until the transistors break down.

3. The method of claim 2, wherein the alternating voltage is applied to respective gates of the test transistors.

4. The method of claim 3, wherein a peak amplitude of the applied alternating voltage is at least 18 volts.

5. The method of claim 4, wherein the peak amplitude is about 22 volts to about 24 volts.

6. The method of claim 2, wherein the alternating voltage has a duty cycle of at most 50%.

7. The method of claim 6, wherein the duty cycle is about 33%.

8. The method of claim 2, wherein the alternating voltage is applied as a plurality of pulses, each pulse having a duration of between about 3 $\mu$s to about 11 $\mu$s, with about 3 $\mu$s to about 4 $\mu$s between pulses.

9. The method of claim 2, wherein the test structure includes a ring oscillator containing a plurality of transistors.

10. The method of claim 2, wherein the step of determining the reliable gate oxide thickness is further based on a ten-year extrapolated life time of the transistor.

\* \* \* \* \*